United States Patent [19]

Adelstein

[11] 4,069,223

[45] Jan. 17, 1978

[54] 4-AMINOMETHYL-1-(3,3,3-TRIARYL-PROPYL)-4-ARYLPIPERIDINE AND DERIVATIVES THEREOF

[75] Inventor: Gilbert W. Adelstein, Evanston, Ill.

[73] Assignee: G. D. Searle & Co., Chicago, Ill.

[21] Appl. No.: 792,616

[22] Filed: May 2, 1977

[51] Int. Cl.$^2$ .................. C07D 401/06; C07D 211/26
[52] U.S. Cl. .................... 260/293.76; 260/293.69; 260/293.78
[58] Field of Search ............. 260/293.69, 293.76, 260/293.78

[56] References Cited

U.S. PATENT DOCUMENTS 3,998,832  12/1976  Adelstein et al. ............. 260/293.54

FOREIGN PATENT DOCUMENTS 691,644  6/1967  Belgium.

Primary Examiner—Norma S. Milestone
Attorney, Agent, or Firm—Dragan J. Karadzic

[57] ABSTRACT

Compounds of the formula

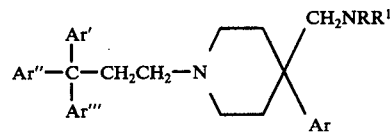

and the non-toxic pharmacologically acceptable acid addition salts thereof; wherein Ar, Ar' and Ar" are each phenyl, halophenyl, or alkylphenyl wherein alkyl contains from 1 to 4 carbon atoms; Ar'" is phenyl, halophenyl, alkylphenyl wherein alkyl contains from 1 to 4 carbon atoms, or pyridyl; R is hydrogen, alkyl having from 1 to 6 carbon atoms, or alkanoyl having from 1 to 6 carbon atoms; and R$^1$ is hydrogen or alkyl having from 1 to 6 carbon atoms. These compounds are antidiarrheal agents characterized by very weak central nervous system activity.

7 Claims, No Drawings

4-AMINOMETHYL-1-(3,3,3-TRIARYLPROPYL)-4-ARYLPIPERIDINE AND DERIVATIVES THEREOF

The present invention is concerned with 4-aminomethyl-1-(3,3,3-triarylpropyl)-4-arylpiperidine and derivatives thereof of the formula

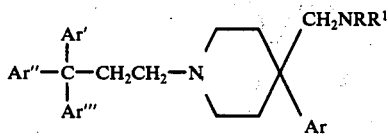

and the non-toxic pharmacologically acceptable acid addition salts thereof; wherein Ar, Ar' and Ar'' are each phenyl, halophenyl, or alkylphenyl wherein alkyl contains from 1 to 4 carbon atoms; Ar''' is phenyl, halophenyl, alkylphenyl wherein alkyl contains from 1 to 4 carbon atoms or pyridyl; R is hydrogen, alkyl having from 1 to 6 carbon atoms, or alkanoyl having from 2 to 6 carbon atoms, and $R^1$ is hydrogen or alkyl having from 1 to 6 carbon atoms.

The alkyls having from 1 to 6 carbon atoms comprehended in the above formula are methyl, ethyl, propyl, butyl, pentyl, hexyl and the branched-chain isomers thereof.

The alkanoyls having from 2 to 6 carbon atoms comprehended in the above formula are acetyl, propionyl, butyryl, pentanoyl, hexanoyl and the branched-chain isomers thereof.

The alkyls having from 1 to 4 carbon atoms contemplated in the alkyphenyl radical in the above formula are exemplified by methyl, ethyl, propyl, butyl and the branched-chain isomers thereof. The alkylphenyl radical encompasses both o-, m-, and p-monoalkylphenyls such as o-tolyl, m-tolyl, p-tolyl, m-ethylphenyl and p-butylphenyl as well as 2,3-, 2,4-, 2,5-, 2,6-, 3,4- and 3,5-dialkylphenyls such as 2,3-dimethylphenyl, 2-methyl-4-ethylphenyl, 2,5-diethylphenyl, 2-methyl-6-propylphenyl, 3,4-dimethylphenyl and 3-methyl-5-ethylphenyl.

The halogens comprehended by the halophenyl radical in the above formula are chlorine, bromine, fluorine and iodine. The halophenyl radical encompasses both o-, m-, and p-monohalophenyls such as o-chlorophenyl, m-bromophenyl and p-fluorophenyl as well as 2,3-, 2,4-, 2,5-, 2,6-, 3,4- and 3,5-dihalophenyls such as 2,3-difluorophenyl, 2,4-dichlorophenyl, 2-chloro-5-bromophenyl, 2-fluoro-6-bromophenyl, 3,4-dibromophenyl and 3-chloro-5-fluorophenyl.

The pyridyl radical comprehended in the above formula can be 2-, 3-, and 4-pyridyl.

The present invention also encompasses optically active compounds prepared by resolving the above compounds which have assymetric centers.

Embodiments of the present invention of the formula

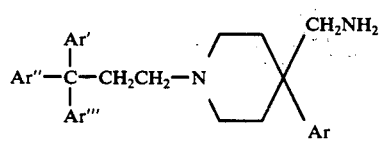

and the non-toxic pharmacologically acceptable acid addition salts thereof; wherein Ar, Ar', Ar'' and Ar''' are as previously defined are preferred, and of these embodiments compounds of the formula

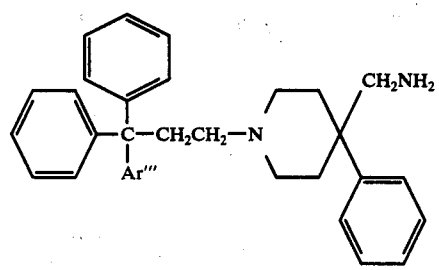

and the non-toxic pharmacologically acceptable acid addition salts thereof; wherein Ar''' is as previously defined are further preferred.

Other preferred embodiments of the present invention are compounds of the formula

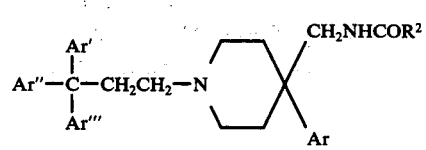

and the non-toxic pharmacologically acceptable acid addition salts thereof; wherein Ar, Ar', Ar'' and Ar''' are as previously defined, and $R^2$ is alkyl having from 1 to 5 carbon atoms, and of these embodiments compounds of the formula

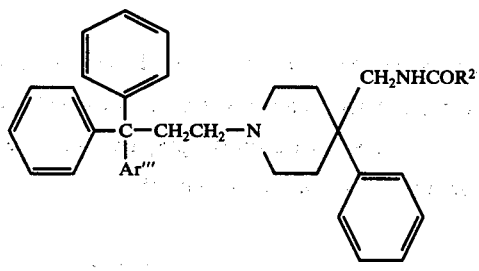

and the non-toxic pharmacologically acceptable acid addition salts thereof; wherein Ar''' and $R^2$ are previously defined are further preferred.

Specifically preferred embodiments are 4-aminomethyl-4-phenyl-1-(3,3,3-triphenylpropyl)piperidine and N-{[4-phenyl-1-(3,3,3-triphenylpropyl)piperidin-4-yl]methyl}-acetamide.

The non-toxic pharamocologically acceptable salts of the aforementioned compounds can be derived from a variety of organic and inorganic acids such as sulfuric, phosphoric, hydrochloric, hydrobromic, hydroiodic, sulfamic, citric, lactic, maleic, succinic, tartaric, cinnamic, acetic, benzoic, gluconic, ascorbic and related acids.

Compounds of the present invention are prepared by methods set out in Scheme I.

SCHEME I
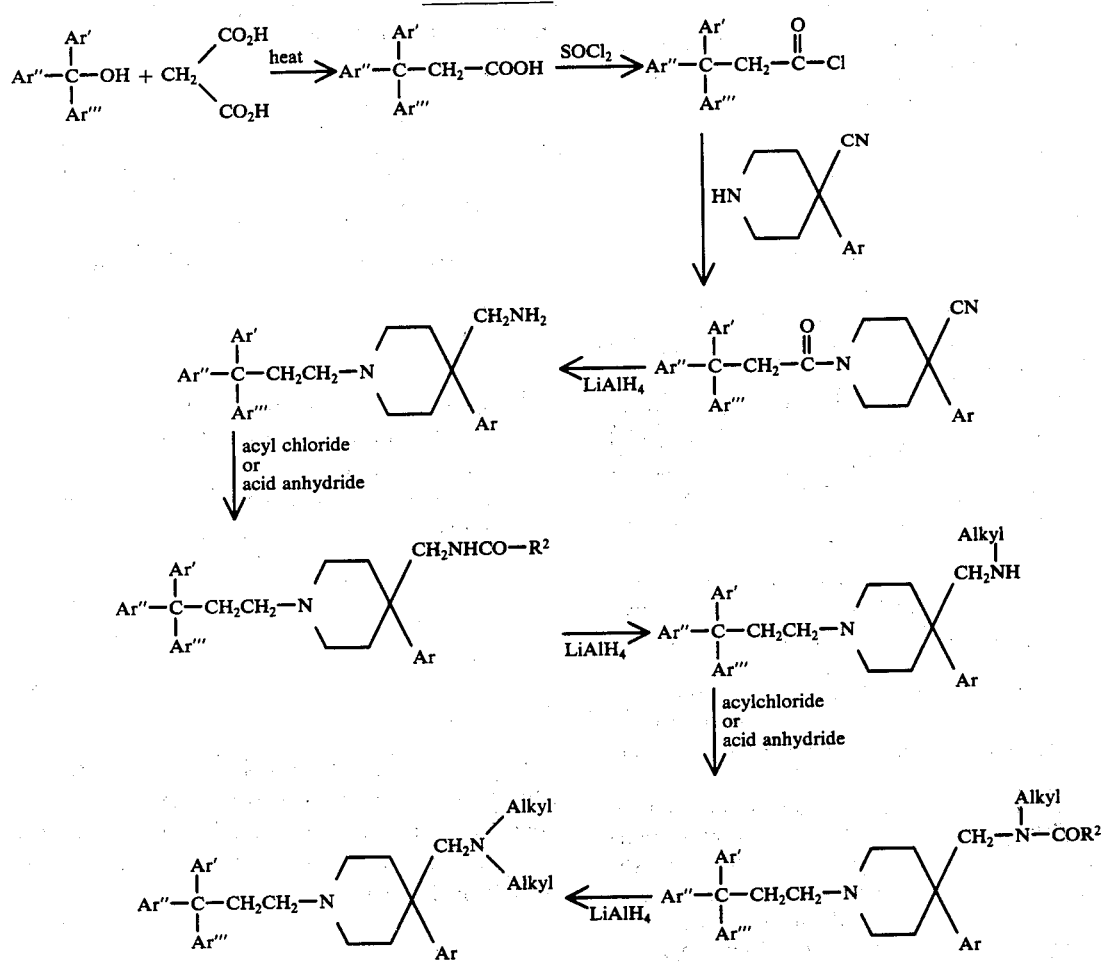
wherein Ar, Ar', Ar'', Ar''', and $R^2$ are as previously defined, and alkyl contains from 1 to 6 carbon atoms.
An alternate process for the preparation of the instant compounds is set out in Scheme II.
SCHEME II
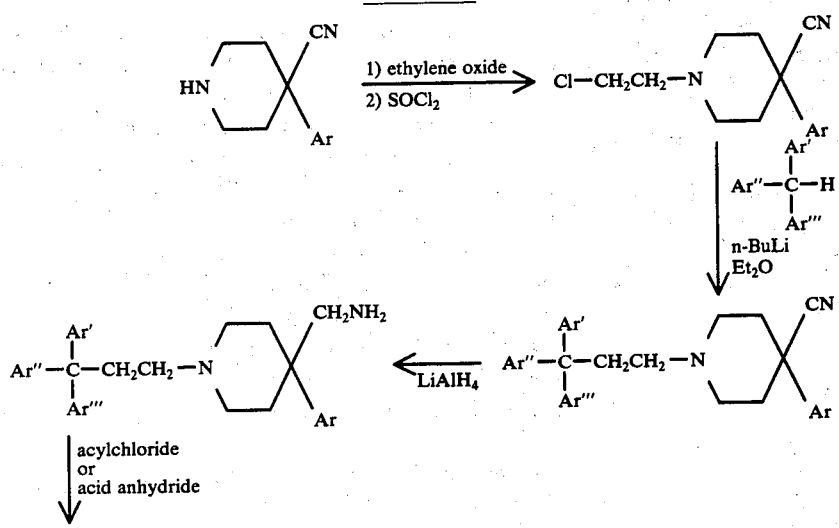

SCHEME II -continued

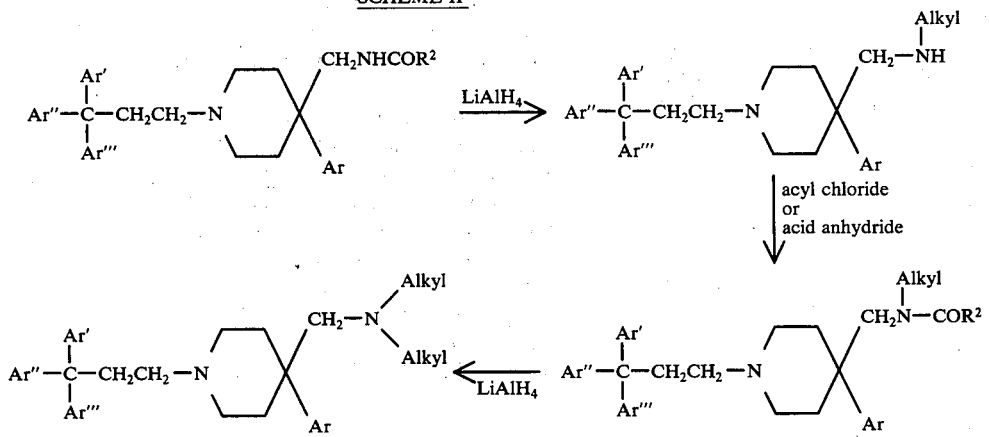

wherein Ar, Ar', Ar", Ar''', R² and Alkyl are as previously defined.

Useful techniques and intermediates are disclosed by S. Patai and Dayogi, J. Chem. Soc. 716 (1962), D. Martensson and E. Nilsson, Acta Chem. Scand. 19(3) 711 (1965) CA-63-6968h. A wide varitey of triphenylcarbinols are prepared by the reaction:

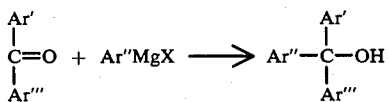

N-(3,3,3-triphenylpropyl)morpholine and N-(3,3,3-triphenylpropyl)piperidine, Martensson and Nilsson, Acta Chem. Scand. 19 (1965), 711–722, and 1-(3,3,3-triphenylpropyl)-4-hydroxymethyl-4-phenylpiperidine and 1-[3,3-diphenyl-3-(3-pyridyl)propyl]-4-hydroxymethyl-4-phenylpiperidine, Gilbert W. Adelstein, et. al., U.S. Pat. No. 3,998,832 issued Dec. 21, 1976, are known compounds. Compounds of the present invention are particularly distinct from the first two of the above compounds by virtue of

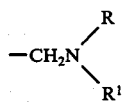

and Ar substituents in the 4 position of the piperidine ring and from the other two compounds by virtue of the

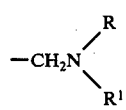

substituent in the 4 position of the piperidine ring.

The compounds of the present invention are useful because of their pharmacological properties. In particular, they possess anti-diarrheal activity with little, if any, central nervous system activity.

The compounds herein described can be combined with pharmaceutically acceptable carriers to provide novel pharmaceutical compositions. The concentration of active ingredient in the composition is not critical, but is preferably 1–80%. These compositions can be administered orally, suitable forms for such administration including tablets, lozenges, capsules, dragees, pills, powders, solutions, suspensions and syrups. Acceptable pharmaceutical carriers are exemplified by gelatin capsules; sugars such as lactose or sucrose; starches such as corn starch or potato starch; cellulose derivatives such as sodium carboxymethyl cellulose, ethyl cellulose, methyl cellulose, or cellulose acetate phthalate; gelatin; talc; calcium phosphates such as dicalcium phosphate or tricalcium phosphate; sodium sulfate; calcium sulfate; polyvinyl pyrrolidone; acacia; polyvinyl alcohol; stearic acid; alkaline earth metal stearates such as magnesium stearate; oils such as peanut oil, cottonseed oil, sesame oil, olive oil, corn oil, oil of theobroma; water; agar; alginic acid; and benzyl alcohol, as well as other non-toxic compatible substances used in pharmaceutical formulations.

The compounds of this invention can be used to produce an antidiarrheal effect in mammals by administering the instant novel compositions containing a therapeutically effective amount of the active ingredient. The term "therapeutically effective amount" is defined as the amount of active ingredient that will produce an antidiarrheal effect, i.e. which will reverse, inhibit or prevent diarrhea. For a particular subject, the amount of active ingredient to be used will vary with the subject involved, the severity of the diarrhea, and the particular active ingredient used. The therapeutically effective amount of a particularly active ingredient is determined by comparing its potency to that of a known standard such as diphenoxylate HCl (Cutting's Handbook of Pharmacology, 4th edition, Appleton-Century Crafts, N.Y. at page 642). Typically 0.1–25 mg/kg is an effective antidiarrheal amount of a given compound.

Anti-diarrheal utility of the instant compounds is evidenced by their ability to inhibit gastrointestinal propulsion as set out in the following tests.

CASTOR OIL INDUCED DIARRHEA IN THE RAT

Adult Charles River male rats were fasted in community cages for 24 hours prior to the test, with free access to water. The compound was administered intragastrically (suspended on 0.5% methycellulose) one hour prior to the administration of castor oil at the dose of 1.0 ml/rat intragastrically. The rats were then observed for the presence or absence of diarrhea, at hourly intervals for up to 8 hours past administration of castor oil. The median effective dose values at each hourly interval were calculated for the compound using the method of Berkson (1953). When tested in the above procedure 4-aminomethyl-1-(3,3,3-triphenylpropyl)-4-phenylpiperidine hydrochloride was found to inhibit gastrointestinal motility. For example:

Comparative Oral Antidiarrheal Potency and Duration of 4-aminomethyl-1-1-(3,3,3-triphenylpropyl)-4-phenylpiperidine hydrochloride (Compound A) to Diphenoxylate hydrochloride in Rat Castor Oil Diarrhea Test.

| Treatment | $ED_{50}$ ± S.E. in mg/kg at Hourly Intervals After Castor Oil | | | | | | |
|---|---|---|---|---|---|---|---|
|  | 2 | 3 | 4 | 5 | 6 | 7 | 8 |
| Diphenoxylate | 0.22 | 0.36 | 0.71 | 1.21 | 1.62 | 1.85 | 1.93 |
| S.E. | 0.04 | 0.11 | 0.14 | 0.20 | 0.28 | 0.28 | 0.32 |
| Potency | 1.0 | 1.0 | 1.0 | 1.0 | 1.0 | 1.0 | 1.0 |
| Compound A | 3.53 | 4.24 | 5.40 | 5.58 | 5.79 | 7.48 | 7.48 |
| S.E. | 0.44 | 0.51 | 0.66 | 0.75 | 0.87 | 2.22 | 2.22 |
| Potency | 0.06 | 0.11 | 0.16 | 0.24 | 0.29 | 0.25 | 0.26 |

CHARCOAL MEAL TEST

Mice Weighing 18-24 grams and previously fasted for 24 hours are each given orally 0.2 ml. of a suspension containing 10% charcoal and 1% methylcellulose. The test compounds are administered intragastrically one hour prior to the charcoal meal. 3.5 Hours after administration of the meal the mice are sacrificed by cervical dislocation and the cecum is examined for the presence or absence of charcoal on an all-or-none basis. Each compound is tested at three dose levels (typically 30, 10, 3 mg/kg) in groups of 6 mice per dose level. Control groups of mice given vehicle only were run concurrently with each test group.

The assessment of the analgesic effect of the present compounds was conducted in the tail clip test.

TAIL CLIP TEST

A specific clip is applied to the base of the tail of the mouse (adult male weighing 18-25 grams) and the time for the animal to turn around to bite at it is measured. The sensitivity of each mouse is determined one-half hour prior to drug administration. Only those mice attempting to bite the clip are included in the experiment. The test compound is then administered intragastrically and the response to placement of the clip is determined at 30, 60, 90 and 120 minutes after treatment. A response is considered positive if the animal takes more than 2 times the pre-drug time to bite at the clip at any of these time intervals. A test compound is considered active when 50 percent or more of the animals used show a positive response. When tested in this procedure 4-aminomethyl-1-(3,3,3-triphenylpropyl)-4-phenyl-piperidine hydrochloride showed weak analgesic effect at 100 mpk.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth temperatures are given in degrees Centigrade (° C), and relative amounts in parts by weight, unless parts by volume is specified. The relationship between parts by weight and parts by volume is the same as that existing between grams and milliliters.

EXAMPLE 1

3 Parts of 3,3,3-triphenylpropionic acid are refluxed with 1 part by volume of thionyl chloride in 25 parts by volume of benzene for about 2 hours. The reaction mixture is then cooled and poured into a mixture of 2.2 parts of 4-phenylisonipecotonitrile hydrochloride, 4.1 parts of potassium carbonate in 20 parts by volume of water and 20 parts by volume of benzene. This reacton mixture is stirred under nitrogen while cooling in an ice bath, and then methylene chloride and water are added to the reaction mixture and the 2-phase system is filtered from the solid which forms. The organic layer is separated, washed with water and with saturated sodium sulfate and dried. The solvent is evaporated to leave an oily residue which is crystallized from ether to afford 4-phenyl-1-(3,3,3-triphenyl-propionyl)isonipecotonitrile melting at about 188.5°–190.5° C. This crystalline product is identical to the aforementioned solid and is represented by the following structural formula

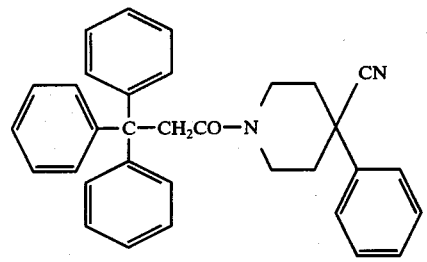

Substitution of the appropriate 3,3,3-triaryl-propionic acid and the appropriate 4-arylisonipecotonitrile in the above detailed procedure affords the following compounds:

1-[3-(o-chlorophenyl)-3,3-diphenylpropionyl]-4-phenylisonipecotonitrile;

1-[3-(m-bromophenyl)-3,3-diphenylpropionyl]-4-phenylisonipecotonitrile;

1-[3-(p-fluorophenyl)-3,3-diphenylpropionyl]-4-phenylisonipecotonitrile;

1-[3-(p-chlorophenyl)-3,3-diphenylpropionyl]-4-phenylisonipecotonitrile;

1-[3,3-bis(p-chlorophenyl)-3-phenylpropionyl]-4-phenylisonipecotonitrile;

1-[3,3-bis(p-fluorophenyl)-3-phenylpropionyl]-4-phenylisonipecotonitrile;

1-[3,3,3-tris(p-chlorophenyl)propionyl]-4-phenyl-isonipecotonitrile;

1-[3,3-bis(p-bromophenyl)-3-(p-chlorophenyl)-propionyl]-4-phenylisonipecotonitrile;

1-[3-(p-chlorophenyl)-3,3-bis(p-fluorophenyl)-propionyl]-4-phenylisonipecotonitrile;

1-[3,3-diphenyl-3-(p-tolyl)propionyl]-4-phenyl-isonipecotonitrile.

1-[3-(p-tert-butylphenyl)-3,3-diphenylpropionyl]-4-phenylisonipecotonitrile;

1-[3-phenyl-3,3-bis(p-tolyl)propionyl]-4-phenyl-isonipecotonitrile;

4-phenyl-1-[3,3,3-tris(p-tolyl)propionyl]-isonipecotonitrile;

1-(3,3,3-triphenylpropionyl)-4-(p-tolyl)isonipecotonitrile;

1-[3-(p-chlorophenyl)-3-phenyl-3-(p-tolyl)propionyl]-4-(p-tolyl)isonipecotonitrile;

4-(m-fluorophenyl)-1-(3,3,3-triphenylpropionyl)isonipecotonitrile;

1-[3-(p-chlorophenyl)-3,3-diphenylpropionyl]-4-(p-chlorophenyl)isonipecotonitrile;

1-[3-(3,4-dichlorophenyl)-3,3-diphenylpropionyl]-4-phenylisonipecotonitrile;

1-[3-(2,3-dimethylphenyl)-3,3-diphenylpropionyl]-4-phenylisonipecotenitrile.

EXAMPLE 2

A mixture of 8.0 parts of 4-phenylisonipecotonitrile, 41.8 parts of 4-methyl-2-pentanone, 4.3 parts of ethylene oxide and 79.2 parts of ethanol is heated in a sealed citric bottle at about 60° C. for 7 days. The resulting solution is cooled, the solvent is evaporated under reduced pressure and the residual material is partitioned between diluted sodium hydroxide and ether. The ether layer is then separated and extracted with diluted HCl. The acid layer is then made alkaline with aqueous sodium hydroxide and the resulting mixture is extracted with ether. The ether layer is dried over sodium sulfate and potassium carbonate and evaporated in vacuum. The residue is crystallized from a mixture of ether and n-pentane to give 1-(2-hydroxyethyl)-4-phenylisonipecotonitrile.

A solution is prepared from 5.9 parts of the nitrile obtained in the preceding paragraph and 134 parts of methylene chloride. This solution is saturated with hydrogen chloride gas at below 10° C. and 5.1 parts of thionyl chloride is added. The mixture is refluxed for 1 hour and then cooled and volatile material is removed under reduced pressure. The residue is dissolved in 88 parts of benzene, and the solution evaporated under reduced pressure. The residue is then crystallized from a mixture of ethanol and ether to give 1-(2-chloroethyl)-4-phenylisonipecotonitrile hydrochloride.

To a solution of 4.4 parts of 2-pyridyldiphenylmethane in 50 parts of cyclohexane is added under nitrogen 8.8 parts by volume of 2.17 molar solution of butyl-lithium in hexane. This solution is stirred at room temperature for 90 minutes and then a solution of 1-(2-chloroethyl)-4-phenylisonipecotonitrile obtained from 5.1 parts of the corresponding hydrochloric salt, in 27 parts of cyclohexane is added and then the mixture is refluxed with stirring for 4 hours. The mixture is cooled, diluted with 71 parts of ether and then washed with water. The organic layer is then extracted with dilute HCl resulting in the precipitation of gum. The aqueous layer is separated from the gum and the organic layer, washed with ether, made strongly alkaline with aqueous NaOH liberating brown-red oil, and extracted with ether. The ether extract is dried over sodium sulfate and evaporated under reduced pressure giving a brown-red gum. This gum is redissolved in ether, treated with Darco, filtered, concentrated and diluted with n-pentane for crystallization. This gives 1-[3,3-diphenyl-3-(2-pyridyl)-propyl]-4-phenylisonipecotonitrile. This compound has the following structural formula

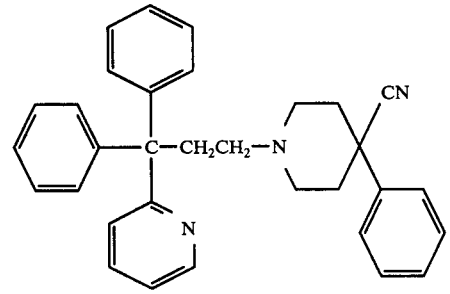

Substitution of the appropriate pyridyldiarylmethane and the appropriate 4-arylisonipecotonitrile in the above detailed procedure affords the following compounds:

1-[3,3-bis(p-fluorophenyl)-3-(3-pyridyl)propyl]-4-phenylisonipecotonitrile;

4-(p-chlorophenyl)-1-[3-chlorophenyl)-1-[3-(p-chlorophenyl)-3-phenyl-3-(3-pyridyl)propyl]-isonipecotonitrile;

1-[3,3-bis(p-tolyl)-3-(3-pyridyl)propyl]-4-(p-tolyl)isonipecotonitrile;

1-[3,3-bis(p chlorophenyl)-3-(3-pyridyl)propyl]-4-(p-tolyl)isonipecotonitrile;

1-[3,3-bis(4-methyl-3-chlorophenyl)-3-(3-pyridyl)-propyl]-4-phenylisonipecotonitrile;

1-[3,3-bis(2,4-dichlorophenyl)-3-(3-pyridyl)propyl]-4-phenylisonipecotonitrile.

EXAMPLE 3

A mixture of 3 parts of 4-phenyl-1-(3,3,3-triphenylpropionyl)isonipecotonitrile and 3 parts of lithium aluminum hydride in 150 parts by volume of tetrahydrofuran is refluxed overnight and then the excess of lithium aluminum hydride is decomposed by the successive addition of 1 part by volume of water, 1 part by volume of 15% sodium hydroxide and 3 parts by volume of water. The mixture is then filtered and the solvent evaporated to afford, as an oil, 4-aminomethyl-4-phenyl-1-(3,3,3-triphenylpropyl)piperidine. This compound is represented by the following structural formula

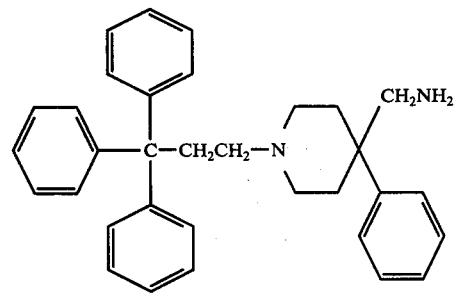

1.9 Part of the compound obtained in the preceding paragraph is dissolved in ether and treated with an excess of hydrogen chloride in 2-propanol. The solid which forms is separated by filtration, washed with ether, and air dried to afford 4-aminomethyl-4-phenyl-1-(3,3,3-triphenylpropyl)piperidine dihydrochloride, melting at about 155°-235° C.

Substitution of the appropriate 4-aryl-1-(3,3,3-triarylpropionyl)isonipecotonitrile or 4-aryl-1-(3,3,3-triarylpropyl)isonipecotonitrile in the above detailed procedure affords the following compounds:

4-aminomethyl-1-[3-(o-chlorophenyl)-3,3-diphenyl-propyl]-4-phenylpiperidine;

4-aminomethyl-1-[3-(m-bromophenyl)-3,3-diphenyl-propyl]-4-phenylpiperidine;

4-aminomethyl-1-[3-(p-fluorophenyl)-3,3-diphenyl-propyl]-4-phenylpiperidine;

4-aminomethyl-1-[3-(p-chlorophenyl)-3,3-diphenyl-propyl]-4-phenylpiperidine;

4-aminomethyl-1-[3,3-bis(p-chlorophenyl)-3-phenyl-propyl]-4-phenylpiperidine;

4-aminomethyl-1-[3,3-bis(p-fluorophenyl)-3-phenyl-propyl]-4-phenylpiperidine;

4-aminomethyl-1-[3,3,3-tris(p-chlorophenyl)propyl]-4-phenylpiperidine;

4-aminomethyl-1-[3,3-bis(p-bromophenyl)-3-(p-chlorophenyl)propyl]-4-phenylpiperidine;

4-aminomethyl-1-[3-(p-chlorophenyl)-3,3-bis(p-fluorophenyl)propyl]-4-phenylpiperidine;

4-aminomethyl-1-[3,3-diphenyl-3-(p-tolyl)propyl]-4-phenylpiperidine;

4-aminomethyl-1-[3-(p-tert-butyphenyl)-3,3-diphenylpropyl]-4-phenylpiperidine; 4-aminomethyl-1-[3-phenyl-3,3-bis(p-tolyl)propyl]-4-phenylpiperidine;

4-aminomethyl-4-phenyl-1-[3,3,3-tris(p-tolyl)propyl]-piperidine;

4-aminomethyl-1-(3,3,3-triphenylpropyl)-4-(p-tolyl)-piperidine;

4-aminomethyl-1-[3-(p-chlorophenyl)-3-phenyl-3-(p-tolyl)propyl]-4-(p-toly)piperidine;

4-aminomethyl-4-(m-fluorophenyl)-1-(3,3,3-triphenylpropyl)piperidine;

4-aminomethyl-1-[3-(p-chlorophenyl)-3,3-diphenyl-propyl]-4-(p-chlorophenyl)piperidine;

4-aminomethyl-1-[3-(3,4dichlorophenyl)-3,3-diphenylpropyl]-4-phenylpiperidine;

4-aminomethyl-1-[3-(2,3-dimethylphenyl)-3,3-diphenylpropyl]-4-phenylpiperidine;

4-aminomethyl-1-[3,3-bis(p-fluorophenyl)-3-(3-pyridyl)]-4-phenylpiperidine;

4-aminomethyl-1-[3,3-diphenyl-3-(2-pyridyl)propyl]-4-phenylpiperidine;

4-aminomethyl-4-(p-chlorophenyl)-1-[3-(p-chlorophenyl)-3-phenyl-3-(3-pyridyl)propyl]piperidine;

4-aminomethyl-1-[3,3-bis(p-tolyl)-3-(3-pyridyl)-propyl]-4-(p-tolyl)piperidine;

4-aminomethyl-1-[3,3-bis(p-chlorophenyl)-3-(3-pyridyl)propyl]-4-(p-tolyl)piperidine;

4-aminomethyl-1-[3,3-bis(4-methyl-3-chlorophenyl)-3-(3-pyridyl)propyl]-4-phenylpiperidine;

4-aminomethyl-1-[3,3-bis(2,4-dichlorophenyl)-3-(3-pyridyl)propyl]-4-phenylpiperidine.

EXAMPLE 4

A mixture of 1 part of 4-aminomethyl-4-phenyl-1-(3,3,3-triphenylpropyl)piperidine dihydrochloride, 1 part by volume of acetic anhydride, 1 part of potassium carbonate, 10 parts by volume of water and 10 parts by volume of methylene chloride is stirred at room temperature for about 4 hours. The organic and aqueous layers are separated, the aqueous layer washed with methylene chloride and the methylene chloride fraction combined with the organic layer. The combined organic fraction is dried over potassium carbonate, the solvent evaporated and the residual colorless amorphous solid crystallized from a mixture of n-hexane and ether to afford N-([4-phenyl-1-(3,3,3-triphenylpropyl)piperidine-4-yl]methyl)acetamide melting at about 154–167° C. This compound is represented by the following structural formula

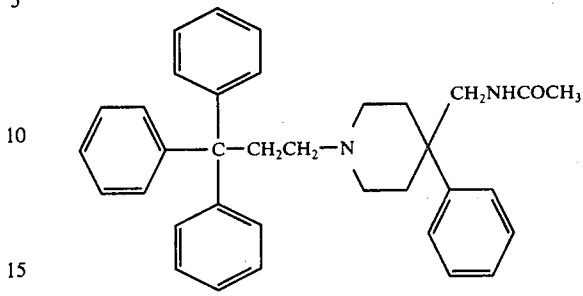

Use of equivalent quantities of the appropriate 4-aminomethyl-4-aryl-1-(3,3,3-triarylpropyl)piperidine and the appropriate carboxylic acid anhydride in the above detailed procedure afforded the following compounds:

N-{[4-phenyl-1-(3,3,3-triphenylpropyl)piperidin-4-yl]methyl}valeramide;

N-{[1-[3-(o-chlorophenyl)-3,3-diphenylpropyl]-4-phenylpiperidin-4-yl]methyl}acetamide;

N-{[1-[3(m-bromophenyl)-3,3-diphenylpropyl]-4-phenylpiperidin-4-yl]methyl}propionamide;

N-{[1-[3-(p-fluorophenyl)-3,3-diphenylpropyl]-4-phenylpiperidin-4-yl]methyl}acetamide;

N-{[1-[3,3-bis(p-chlorophenyl)-3-phenylpropyl]-4-phenylpiperidin-4-yl]methyl}butyramide.

N-{[1-[3,3,3-tris(p-chlorophenyl)propyl]-4-phenyl-piperidin-4-yl]methyl}acetamide;

N-{[1-[3,3-bis(p-bromophenyl)-3-(p-chlorophenyl)-propyl]-4-phenylpiperidin-4-yl]methyl}acetamide;

N-{[1-[3,3-diphenyl-3-(p-toly)propyl]-4-phenyl-piperidin-4-yl]methyl}acetamide;

N-{[1-[3-phenyl-3,3-bis(p-tolyl)propyl]-4-phenyl-piperidin-4-yl]methyl}propionamide;

N-{[4-phenyl-1-[3,3,3-tris(p-tolyl)propyl]piperidin-4-yl]methyl}propionamide;

N-{[1-(3,3,3-triphenylpropyl)-4-(p-tolyl)piperidin-4-yl]methyl}butyramide;

N-{[1-[3-(p-chlorophenyl)-3-phenyl-3-(p-tolyl)-propyl]-4(p-tolyl)piperidin-4-yl]methyl}acetamide;

N-{[4-(m-fluorophenyl)-1-(3,3,3-triphenylpropyl)-piperidin-4-yl]methyl}acetamide.

N-{[1-[3-(p-chlorophenyl)-3,3-diphenylpropyl]-4-(p-chlorophenyl)piperidin-4-yl]methyl}acetamide;

N-{[1-[3-(3,4-dichlorophenyl)-3,3-diphenylpropyl]4-phenylpiperidin-4-yl]methyl}acetamide;

N-{[1-[3-(2,3-dimethylphenyl)-3,3-diphenylpropyl]4-phenylpiperidin-4-yl]methyl{acetamide;

N-{[1-[3,3-bis(p-fluorophenyl)-3-(3-pyridyl)propyl]-4-phenylpiperidin-4-yl]methyl}acetamide;

N-{[1-[3,3-diphenyl-3-(2-pyridyl)propyl]-4-phenyl-piperidin-4-yl]methyl}propionamide;

N-{[4-(p-chlorophenyl)-1-[3-chlorophenyl)-3-phenyl-3-(3-pyridyl)propyl]piperidin-4-yl]methyl}acetamide;

N-{[1-[3,3-bis(p-tolyl)-3-(3-pyridyl)propyl]-4-(p-tolyl)piperidin-4-yl]methyl}acetamide;

N-{[1-[3,3-bis(p-chlorophenyl)-3-(3-pyridyl)propyl]-4-(p-tolyl)piperidine-4-yl]methyl}acetamide;

N-{[1-[3,3-bis(4-methyl-3-chlorophenyl)-3-(3-pyridyl)propyl]-4phenylpiperidin-4-yl]methyl}acetamide;

N-{[1-[3,3-bis(2,4-dichlorophenyl)-3-(3-pyridyl)-propyl]-4-phenylpiperidin-4-yl]methyl}acetamide.

EXAMPLE 5

Substitution of an equivalent quantity of the appropriate N-{[1-(3,3,3-triarylpropyl)-4-arylpiperidin-4-yl]methyl}carboxylic acid amide for 4-phenyl-1-(3,3,3-triphenylpropionyl)isonipecotonitrile called for in Example 3 and substantial repetition of the procedure detailed in that example affords the following compounds:

4-(ethylaminomethyl)-4-phenyl-1-(3,3,3-triphenylpropyl)piperidine;

4-(pentylaminomethyl)-4-phenyl-1-(3,3,3-triphenylpropyl)piperidine;

4-(ethylaminomethyl)-1-[3-(o-chlorophenyl)-3,3-diphenylpropyl]-4-phenylpiperidine;

4-(butylaminomethyl)-1-[3,3-bis(p-chlorophenyl)-3-phenylpropyl]-4-phenylpiperidine;

4-(ethylaminomethyl)-1-[3,3,3-tris(p-chlorophenyl)-propyl]-4-phenylpiperidine;

1-[3-phenyl-3,3-bis(p-tolyl)propyl]-4-phenyl-4-(propylaminomethyl)piperidine;

4-phenyl-4-(propylaminomethyl)-1-[3,3,3-tris(p-tolyl)propyl]piperidine;

1-[3-(p-chlorophenyl)-3-phenyl-3-(p-tolyl)propyl]4-(ethylaminomethyl)-4-(p-tolyl)piperidine;

4-(ethylaminomethyl)-4-(m-fluorophenyl)-1-(3,3,3-triphenylpropyl)piperidine;

4-(ethylaminomethyl)-1-[3-(3,4-dichlorophenyl)-3,3-diphenylpropyl]-4-phenylpiperidine;

4-(ethylaminomethyl)-1-[3-(2,3-dimethylphenyl)-3,3-diphenylpropyl]-4-phenylpiperidine;

1-[3,3-diphenyl-3-(2-pyridyl)propyl]-4-phenyl-4-(propylaminomethyl)piperidine;

4-(p-chlorophenyl)-1-[3-(p-chlorophenyl)-3-phenyl-3-(3-pyridyl)propyl]-4-(ethylaminomethyl)piperidine;

4-(ethylaminomethyl)-1-[3,3-bis(p-tolyl)-3-(3-pyridyl)propyl]-4-(p-tolyl)piperidine;

1-[3,3-bis(p-chlorophenyl)-3-(3-pyridyl)propyl]-4-(ethylaminomethyl)-4-(p-tolyl)piperidine;

1-[3,3-bis(2,4-dichlorophenyl)-3-(3-pyridyl)propyl]-4-(ethylaminomethyl)-4-phenylpiperidine.

EXAMPLE 6

To a solution of 5.5 parts of 4-aminomethyl-4-phenyl-1-(3,3,3-triphenylpropyl)piperidine in 30 parts of 90% formic acid is added 16.2 parts of formalin. After evolution of carbon dioxide subsides, the mixture is heated on a steam bath for about 8 hours. The excess solvent is then evaporated, the residue taken up in ether and the ether solution washed twice with water. The ether solution is then dried over anhydrous sodium sulfate and acidified with hydrogen chloride gas to afford 4-(dimethylaminomethyl)-4-phenyl-1-(3,3,3-triphenylpropyl)piperidine dihydrochloride. This compound is represented by the following structural formula.

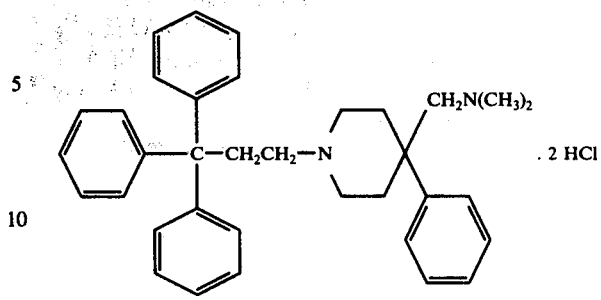

EXAMPLE 7

When the appropriate 4-(alkylaminomethyl)-1-(3,3,3-triarylpropyl)-4-arylpiperidine is reacted with the appropriate carboxylic acid anhydride according to the procedure detailed in Example 4 and the thus obtained product is then treated with lithium aluminum hydride according to the procedure of Example 3 the following compounds are obtained:

4-(diethylaminomethyl)-4-phenyl-1-(3,3,3-triphenylpropyl)piperidine;

4-(ethylpentylaminomethyl)-4-phenyl-1-(3,3,3-triphenylpropyl)piperidine;

4-(diethylaminomethyl)-1-[3-(o-chlorophenyl)-3,3-diphenylpropyl]-4-phenylpiperidine;

4-(dibutylaminomethyl)-1-[3,3-bis(p-chlorophenyl)-3-phenylpropyl]-4-phenylpiperidine;

4-(ethylpropylaminomethyl)-1-[3,3,3-tris(p-chlorophenyl)propyl]-4-phenylpiperidine;

1-[3-phenyl-3,3-bis(p-tolyl)propyl]-4-phenyl-4-(dipropylaminomethyl)piperidine;

4-phenyl-4-(dipropylaminomethyl)-1-[3,3,3-tris(p-tolyl)propyl]piperidine;

1-[3-(p-chlorophenyl)-3-phenyl-3-(p-tolyl)propyl]-4-(diethylaminomethyl)-4-(p-tolyl)piperidine;

4-(diethylaminomethyl)-4-(m-fluorophenyl)-1-(3,3,3-triphenylpropyl)piperidine;

4-(diethylaminomethyl)-1-[3-(3,4-dichlorophenyl)-3,3-diphenylpropyl]-4-phenylpiperidine;

4-(diethylaminomethyl)-1-[3-(2,3-dimethylphenyl)-3,3-diphenylpropyl]-4-phenylpiperidine;

1-[3,3-diphenyl-3-(2-pyridyl)propyl]-4-phenyl-4-(dipropylaminomethyl)piperidine;

4-(p-chlorophenyl)-1-[3-(p-chlorophenyl)-3-phenyl-3-(3-pyridyl)propyl]-4-(diethylaminomethyl)piperidine;

4-(diethylaminomethyl)-1-[3,3-bis(p-tolyl)-3-(3-pyridyl)propyl]-4-(p-tolyl)piperidine;

1-[3,3-bis(p-chlorophenyl)-3-(3-pyridyl)propyl]-4-(diethylaminomethyl)-4-(p-tolyl)piperidine; and 1-[3,3-bis(2,4-dichlorophenyl)-3-(3-pyridyl)propyl]-4-(diethylaminomethyl)-4-phenylpiperidine;

What is claimed is:

1. A compound of the formula

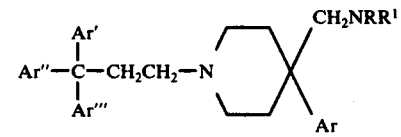

and the non-toxic pharmacologically acceptable acid addition salts thereof; wherein Ar, Ar' and Ar" are each phenyl, halophenyl or alkylphenyl wherein alkyl contains from 1 to 4 carbon atoms; Ar''' is phenyl, halophenyl, alkylphenyl wherein alkyl contains from 1 to 4 carbon atoms or pyridyl; R is hydrogen, alkyl having from from 1 to 6 carbon atoms or alkanoyl having from 2 to 6 carbon atoms; and R¹ is hydrogen or alkyl having from 1 to 6 carbon atoms.

2. A compound according to claim 1 having the formula

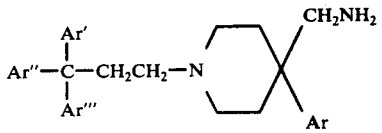

and the non-toxic pharmacologically acceptable acid addition saltsthereof; wherein Ar, Ar' and Ar¹ are each phenyl, halophenyl, or alkylphenyl wherein alkyl contains from 1 to 4 carbon atoms; and Ar''' is phenyl, halophenyl, alkylphenyl wherein alkyl contains from 1 to 4 carbon atoms, or pyridyl.

3. A compound according to claim 1 having the formula

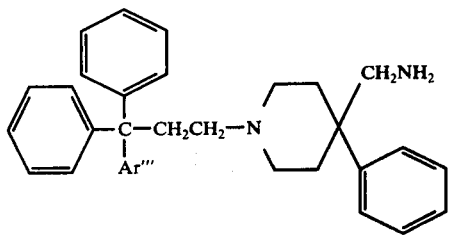

and the non-toxic pharmacologically acceptable acid addition salts thereof; wherein Ar''' is phenyl, halophenyl, alkylphenyl wherein alkyl contains from 1 to 4 carbon atoms or pyridyl.

4. A compound according to claim 1 having the formula

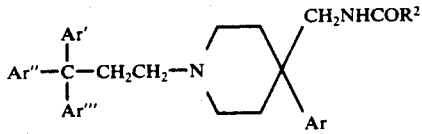

and the non-toxic pharmacologically acceptable acid addition salts thereof; wherein Ar, Ar' and Ar'' are each phenyl, halophenyl or alkylphenyl wherein alkyl contains from 1 to 4 carbon atoms; Ar''' is phenyl, halophenyl, alkylphenyl wherein alkyl contains from 1 to 4 carbon atoms, or pyridyl; and R₂ is alkyl having from 1 to 5 carbon atoms.

5. A compound according to claim 1 having the formula

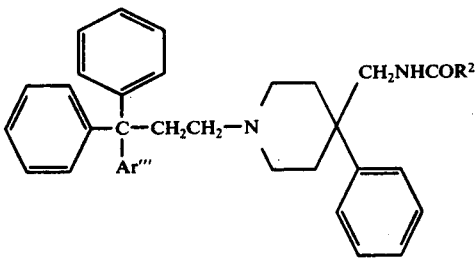

and the non-toxic pharmacologically acceptable acid addition salts thereof; wherein Ar''' is phenyl, halophenyl, alkylphenyl wherein alkyl contains from 1 to 4 carbon atoms, or pyridyl; and R² is alkyl having from 1 to 5 carbon atoms.

6. A compound according to claim 1 which is 4-amino-methyl-4-phenyl-1-(3,3,3-triphenylpropyl)piperidine.

7. A compound according to claim 1 which is N-{[4-phenyl-1-(3,3,3-triphenylpropyl)piperidine-4-yl[methyl}acetamide.

* * * * *